United States Patent
Boehm et al.

(10) Patent No.: US 9,808,801 B2
(45) Date of Patent: Nov. 7, 2017

(54) ROTATABLE CARTRIDGE FOR MEASURING A PROPERTY OF A BIOLOGICAL SAMPLE

(71) Applicant: Roche Diagnostics Operations, Inc., Indianapolis, IN (US)

(72) Inventors: Christoph Boehm, Viernheim (DE); Sascha Lutz, Neustadt (DE); Thomas Dolbinow, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/343,389

(22) Filed: Nov. 4, 2016

(65) Prior Publication Data

US 2017/0050185 A1 Feb. 23, 2017

Related U.S. Application Data

(63) Continuation of application No. PCT/EP2015/060013, filed on May 7, 2015.

(30) Foreign Application Priority Data

May 13, 2014 (EP) .................................... 14168042

(51) Int. Cl.
*G01N 21/07* (2006.01)
*G01N 35/00* (2006.01)
(Continued)

(52) U.S. Cl.
CPC ..... *B01L 3/50273* (2013.01); *B01L 3/502715* (2013.01); *B01L 3/502738* (2013.01);
(Continued)

(58) Field of Classification Search
CPC ........... G01N 21/07; G01N 35/00; B01L 3/00
(Continued)

(56) References Cited

U.S. PATENT DOCUMENTS 4,812,294 A * 3/1989 Combs .................... B01L 3/502
422/533
6,309,875 B1 * 10/2001 Gordon .................... B04B 5/02
422/50
(Continued)

FOREIGN PATENT DOCUMENTS

WO 2014/041364 A1 3/2014

OTHER PUBLICATIONS

International Search Report pertaining to PCT/EP2015/060013 dated May 7, 2015, 4 pages.
Written Opinion pertaining to PCT/EP2015/060013 dated May 7, 2015, 6 pages.

*Primary Examiner* — Arlen Soderquist
(74) *Attorney, Agent, or Firm* — Dinsmore & Shohl LLP

(57) ABSTRACT

A cartridge for an automatic analyzer, formed from a cover and carrier structure, is operable for rotation about an axis and has at least one container with at least one reservoir containing at least one fluid. Each container may rotate about the axis within a cavity and relative to the carrier structure. A piercing structure opens a seal of each reservoir when the container rotates relative to the carrier structure. Each container and each cavity has a frictional element that mate and cause friction. Each container has an engaging surface which mates with an engaging surface of a rotational actuator that applies torque to rotate and open the container via the piercing structure. A fluidic structure of the cartridge processes a biological sample into a processed biological sample and enables via a measurement structure measurement of the processed biological sample. A duct is between the cavity and the fluidic structure.

26 Claims, 13 Drawing Sheets

(51) Int. Cl.
*B01L 3/00* (2006.01)
*G01N 35/10* (2006.01)

(52) U.S. Cl.
CPC ... *G01N 35/00069* (2013.01); *G01N 35/1079* (2013.01); *B01L 2300/041* (2013.01); *B01L 2300/044* (2013.01); *B01L 2300/0645* (2013.01); *B01L 2300/0672* (2013.01); *B01L 2300/0803* (2013.01); *B01L 2300/087* (2013.01); *B01L 2300/0858* (2013.01); *B01L 2300/16* (2013.01); *B01L 2400/0409* (2013.01); *B01L 2400/0683* (2013.01)

(58) Field of Classification Search
USPC .............................................. 422/72; 436/45
See application file for complete search history.

(56) References Cited

U.S. PATENT DOCUMENTS

| | | | |
|---|---|---|---|
| 7,688,449 B2* | 3/2010 | Ogawa | B01L 3/50273 356/442 |
| 2003/0219890 A1* | 11/2003 | Gordon | B01F 15/0233 435/287.2 |
| 2004/0116686 A1 | 6/2004 | Akashi et al. | |
| 2004/0131500 A1* | 7/2004 | Chow | G01N 11/14 422/72 |
| 2005/0169804 A1* | 8/2005 | Moore | G01N 21/07 422/72 |
| 2007/0065346 A1 | 3/2007 | Henry et al. | |
| 2011/0085950 A1* | 4/2011 | Lee | B01L 3/50273 422/504 |
| 2012/0291538 A1 | 11/2012 | Ludowise et al. | |
| 2013/0344617 A1 | 12/2013 | Robertson et al. | |

* cited by examiner

ROTATABLE CARTRIDGE FOR MEASURING A PROPERTY OF A BIOLOGICAL SAMPLE

CROSS-REFERENCE TO RELATED APPLICATIONS

This application is a continuation of International Application No. PCT/EP2015/060013, filed May 7, 2015, which claims priority to European patent application No. EP14168042.1, filed May 13, 2014.

TECHNICAL FIELD

The invention relates to analytical test devices for biological samples, in particular to the design and use of rotatable cartridges for performing a measurement on of a biological sample.

BACKGROUND AND RELATED ART

Two classes of analysis systems are known in the field of medical analysis: wet analysis systems, and dry-chemical analysis systems. Wet analysis systems, which essentially operate using "wet reagents" (liquid reagents), perform an analysis via a number of required step such as, for example, providing a sample and a reagent into a reagent vessel, mixing the sample and reagent together in the reagent vessel, and measuring and analyzing the mixture for a measurement variable characteristic to provide a desired analytical result (analysis result). Such steps are often performed using technically complex, large, line-operated analysis instruments, which allow required manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and dissolved reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, and some of them are portable and battery-operated. The systems are used for decentralized analysis, for example, at resident physicians, on the wards of the hospitals, and in so-called "home monitoring" during the monitoring of medical-analytic parameters by the patient himself (in particular blood glucose analysis by diabetics or coagulation status monitoring by warfarin patients).

In wet analysis systems, the high-performance analysis instruments allow the performance of more complex multistep reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the probe can first be transported through a porous solid matrix, which contains a specific binding reagent for the analyte. A marking reagent can subsequently be caused to flow through the porous matrix, to mark the bound analyte and allow its detection. To achieve precise analysis, a washing step must previously be performed, in which unbound marking reagent is completely removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control is especially frequently performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping. Microstructures, which are generated by lithography methods, increasingly being used more recently, however.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

U.S. Pat. No. 8,114,351 B2 discloses an analysis system for the analysis of a body fluid sample for an analyte. The analysis system provides a test element and an analysis instrument having a dosing station and a measurement station. The test element has a housing an (at least) one sample analysis channel enclosed by the housing. The test element is rotatable around an axis of rotation which extends through the test element.

U.S. Pat. No. 8,470,588 B2 discloses a test element and a method for detecting an analyte. The test element is essentially disk shaped and flat, and can be rotated about a preferably central axis which is perpendicular to the plane of the disk shaped test element.

Kim, Tae-Hyeong, et al. "Flow-enhanced electrochemical immunosensors on centrifugal microfluidic platforms." Lab on a Chip 13.18 (2013): 3747-3754, doi:10.1039/c3lc50374g, (hereafter "Kim et. al.") discloses a fully integrated centrifugal microfluidic device with features for target antigen capture from biological samples, via a bead-based enzyme-linked immune-sorbent assay, and flow-enhanced electrochemical detection. This is integrated into a Centrifugal microfluidic discs, also known as "lab-on-a-disc" or microfluidic CDs.

Martinez-Duarte, Rodrigo, et al. "The integration of 3D carbon-electrode dielectrophoresis on a CD-like centrifugal microfluidic platform." Lab on a Chip 10.8 (2010): 1030-1043, doi:10.1039/6925456K, (hereafter "Martinez-Duarte et. al.") discloses a dielectrophoresis (DEP)-assisted filter with a compact disk (CD)-based centrifugal platform. 3D carbon electrodes are fabricated using the C-MEMS technique and are used to implement a DEP-enabled active filter to trap particles of interest.

International patent application WO 2014/041364 discloses a sample metering device for a liquid sample comprises at least one capillary passage with a first inlet for receiving sample, and an outlet; a side passage extending from the capillary passage part way along the length thereof and leading to the outlet; and a second inlet located between the first inlet and intersection with the side passage. A fluid application region for receiving a liquid sample to be tested is provided for entry to the capillary passage via the first inlet, and a second fluid application region is provided for entry of fluid such as chase buffer to the capillary passage. The second inlet prevents any excess sample in the well entering the capillary passage when chase buffer is applied.

United States patent application publication US 2013/0344617 A1 discloses a sample metering device for a liquid sample comprises at least one capillary passage with an inlet and an outlet; a side passage extending from the capillary passage part way along the length thereof and leading to an outlet; a fluid application region for receiving a liquid sample to be tested, for entry to the capillary passage via the inlet; first sealing means operable releasably to seal the outlet of the capillary passage; and second sealing means operable releasably to seal the outlet of the side passage.

United States patent application publication US 2012/0291538 A1 discloses a system and method for volumetric metering on a sample processing device. The system can include a metering reservoir, and a waste reservoir positioned in fluid communication with a first end of the metering reservoir to catch excess liquid from the metering reservoir that exceeds a selected volume. The system can further include a capillary valve in fluid communication with the second end of the metering reservoir to inhibit liquid from exiting the metering reservoir until desired. The method can include metering the liquid by rotating the sample processing device to exert a first force on the liquid that is insufficient to move the liquid into the capillary valve, and rotating the sample processing device to exert a second force on the liquid that is greater than the first force to move the metered volume of the liquid to the process chamber via the capillary valve.

United States patent application publication US 2004/011686 A1 discloses a nucleic acid refining apparatus, being ease in automation thereof, keeping high in contacting frequency between nucleic acid within a sample and a solid phase during nucleic acid capture processing, thereby proving high capturing rate, comprises: means for separating a liquid containing the nucleic acid therein from said sample through centrifugal force; means for transferring a reagent through the centrifugal force; means for producing a mixture liquid of said reagent transferred through the centrifugal force and a solution containing said nucleic acid therein; a carrier for capturing said nucleic acid; means for transferring said mixture liquid to said carrier through the centrifugal force; heating means for heating said carrier; and a holding means for separating and holding the reagent containing said nucleic acid eluting from said carrier.

SUMMARY

The invention provides for a method of performing a measurement, a cartridge for an automatic analyzer, and an automatic analyzer in the independent claims. Embodiments are given in the dependent claims. The measurement may for example be an optical measurement or an electrical measurement.

In one aspect the invention provides for a method of performing a measurement of a processed biological sample using a cartridge.

A cartridge as used here encompasses a test element for processing the biological sample into a processed biological sample. The cartridge may include structures or components which enable a measurement to be performed on the biological sample. A cartridge is a test element as is defined and explained in U.S. Pat. Nos. 8,114,351 B2 and 8,470,588 B2. A cartridge as used herein may also be referred to as a Centrifugal microfluidic disc, also known as "lab-on-a-disc" or a microfluidic CD.

A biological sample as used herein encompasses as chemical product derived, copied, replicated, or reproduced from a sample taken from an organism.

The cartridge is operable for being spun around a rotational axis. The cartridge further comprises at least one container with at least one fluid reservoir containing at least one fluid. In some examples the cartridge may have more than one container. In some examples each container has one fluid reservoir and in other examples each container may have more than one fluid reservoir. Different fluid reservoirs within the same cartridge may each contain the same fluid or one or more of the reservoirs may contain a different fluid. The cartridge comprises a cavity for each of the at least one container. The cartridge may also comprise at least a common cavity for two or more containers. The at least one container is configured to rotate about the rotational axis of the cartridge within the cavity. In some examples the rotational axis will go through the cavity. In this case the container rotates about this axis, which is directly inside of the cavity. In other examples the rotational axis is outside of the cavity. In this case the particular container is constrained such that it moves within the cavity such that it rotates about the rotational axis.

The at least one container is configured to rotate relative to the cartridge. Each of the at least one fluid reservoir comprises a pierceable seal. The pierceable seal seals each fluid reservoir so that the fluid does not come out. Piercing the pierceable seal allows the fluid to exit a particular fluid reservoir. The cavity comprises at least one piercing structure for each of the at least one fluid reservoir. The at least one piercing structure is configured to open the seal by piercing the pierceable seal when the at least one container is rotated relative to the cartridge. Each container is within a cavity. Each cavity can comprise one container or multiple containers. In the later case, multiple containers share a common cavity. Within each cavity there is a piercing structure for each pierceable seal. Rotating a particular container about the rotational axis and relative to the cartridge causes it to move into a position where the pierceable seal will be pierced by the piercing structure causing the particular fluid reservoir to open.

The at least one container comprises a first frictional element and the cavity comprises a second frictional element. The first frictional element mates with the second frictional element. The first frictional element and the second frictional element are configured for causing friction between the cavity and the at least one container. The first and second frictional elements cause friction which prevents a particular container from rotating about the rotational axis when it is not supposed to. The at least one container comprises a first engaging surface operable for mating with a second engaging surface of a rotational actuator operable for applying torque to the at least one container. The rotational actuator is used to deliberately move the container in a controlled fashion relative to the cartridge such that the piercing structure is brought into contact with the pierceable seal. This relative movement can be achieved either by fixing the container using the rotational actuator and rotating the cartridge such that the piercing structure is brought into contact with the pierceable seal or by fixing the cartridge and rotating the container using the rotational actuator such that the piercing structure is brought into contact with the pierceable seal or by rotating the container using the rotational actuator with a different rotational rate than the cartridge such that the piercing structure is brought into contact with the pierceable seal.

The cartridge further comprises a fluidic structure for processing a biological sample into the processed biological sample. For instance the cartridge may comprise an entrance or place (sample port) where a biological sample can be deposited into the cartridge such that it reaches the fluidic structure. The cartridge further comprises a duct between the cavity and the fluidic structure. The duct may enable the fluid originally stored in the fluid reservoir to leave the cavity and enter the fluidic structure. The duct may be implemented in several different ways. For instance the cavity could be closer to the rotational axis than the fluidic structure. Then by rotating the cartridge the fluid could be forced through the duct and into the fluidic structure. In other cases the fluid reservoir may empty the fluid into a cavity where a siphon then causes the fluid to enter the fluidic structure.

The fluidic structure comprises structure for enabling the measurement of the processed biological sample. The fluidic structure is configured for receiving the biological sample.

The method comprises the step of placing the biological sample into the fluidic structure. The method further comprises the step of applying the torque to the at least one container using the rotational actuator to overcome the friction between the cavity and the at least one container and rotate the at least one container relative to the cartridge around the rotational axis of the cartridge to open the pierceable seal. Rotating the at least one container relative to the cartridge causes the at least one piercing structure to open the seal by piercing the pierceable seal.

The method further comprises the step of controlling the rotational rate of the cartridge to process the biological sample into the processed biological sample using the fluidic structure. The method further comprises the step of controlling the rotational rate of the cartridge to force the at least one fluid through the duct and through at least a portion of the fluidic structure. The friction between the cavity and the at least one container causes the at least one container to rotate around the rotational axis at the same rate as the cartridge if the rotational actuator is not in engagement with the container The method further comprises performing the measurement using the measurement structure and using a measurement system. It should be noted that the first step of the method is placing the biological sample into the fluidic structure and the last step is performing the measurement. However, the other steps in the method may be performed in a different order and various steps may be performed more than once. For instance the cartridge may have more than one container and a particular container may have more than one fluid reservoir. As such the torque may be applied to different containers at different times to release the different fluids and also the particular order of when the biological sample is processed into the processed biological sample may occur differently in different cartridges for different test regimes.

This embodiment may possibly have one or more of the following advantages listed in this paragraph: It may provide protection of the container against mechanical damages (e.g. during transportation or storage). It may provide protection of the container against unwanted contact by the user (the relative rigid cover prevents pressing and thereby unintentionally opening the container by the user). It may provide for a fixed and non-exchangeable combination of container and disc. This may guaranty the "fit" or usability of reagents on the disc and reagents within the reservoir. This in turn may improve the reliability of test results (user cannot exchange the containers) or in confidence that the test results were obtained properly.

The fluidic structure may be a micro-fluidic structure.

The measurement may include, but is not limited to: a photometric transmission measurement, a measurement of the scattering of light, a chemiluminescence, a fluorescence, a Total Internal Reflection Fluorescence (TIRF), and electrochemiluminescense (ECL) measurement.

The pierceable seal could for example by a thin film or a foil. For example a small piece of metal foil or a thin film of plastic may be used as the pierceable seal. The piercing structure may be any structure which is capable of piercing the particular pierceable seal and for instance could be a pin, a lance, or a sharp edge.

Each fluid reservoir may be filled with a fluid. If there are multiple reservoirs in a particular cartridge more than one fluid reservoir may have the same fluid. However, different fluid reservoirs may also have different fluids.

A rotational actuator as used herein is an actuator which is used or configured for applying torque to one or more container in the cartridge so as to rotate it relative to the cartridge about the rotational axis. In some examples the rotational actuator may be a device or apparatus which holds a particular container in a fixed position as the cartridge is rotated. In other examples the rotational actuator may for instance be mounted on a clutch or other mechanism such that the rotational actuator rotates with the cartridge. The rotational actuator would then further be configured such that as it is rotating with the cartridge it causes a further rotation of the container relative to the cartridge.

In another embodiment the measurement structure is a transparent structure. The transparent structure may for example be a window. The transparent structure may also be optically transparent. In another example the transparent structure has more than one transparent and/or optical component. For example on one side one face of the container there may be a window and the other there may be a mirror. The optically transparent structure may for instance be a hole in one or both sides of the cartridge. The transparent structure may also comprise an optical filter. A transparent structure may also encompass being transparent outside of the visible range such as in the near infrared or near ultraviolet range. The optical measurement as used herein may also encompass measurements in the near infrared or near ultraviolet range. In other examples optically transparent may exclude the near infrared or near ultraviolet range.

In other examples the measurement structure comprises two or more electrodes for making an electrical measurement or ECL measurement of the processed biological sample. For example the measurement structures of Martinez-Duarte et. al. or Kim et. al. may be incorporated into a cartridge.

An advantage of such a method is that the at least one fluid reservoir can be opened at a particular time before, during and after the processing of the biological sample into the processed biological sample. Also fluid may be released more than once and more than one type of fluid may be used. This may enable more flexible and complicated methods of processing a biological sample into a processed biological sample. It may also reduce the amount of instrumentation necessary to do this. For instance the use of the containers inside the cartridge may eliminate the need to use dosing needles to dispense the at least one fluid to the cartridge.

In another aspect the invention provides for a cartridge for an automatic analyzer. The cartridge is operable for being spun around a rotational axis. The cartridge further comprises at least one container with at least one fluid reservoir containing at least one fluid. The cartridge comprises a cavity for each of the at least one container. The at least one container is configured to rotate about the rotational axis of the cartridge within the cavity. The at least one container is configured to rotate relative to the cartridge. Each of the at least one fluid reservoir comprises a pierceable seal. The cavity comprises at least one piercing structure for each of the at least one fluid reservoir. The at least one piercing structure is configured to open the seal by piercing the pierceable seal when the at least one container is rotated relative to the cartridge.

The at least one container comprises a first frictional element and the cavity comprises a second frictional element. The first frictional element mates with the second frictional element. The first frictional element and the second frictional element are configured for causing friction between the cavity and the at least one container. The at least one container comprises a first engaging surface operable for mating with the second engaging surface of a rotational actuator operable for applying torque to the at least one container. The cartridge comprises a fluidic structure for processing a biological sample into the processed biological sample. The cartridge comprises a duct between the cavity and the fluidic structure. The fluidic structure comprises optionally a transparent structure for enabling an optical measurement of the processed biological sample. The fluidic structure is configured for receiving the biological sample.

This cartridge and other cartridges described herein may have the advantage of being able to provide at least one fluid into the fluidic structure without the use of an external dosing needle or system.

In another embodiment the cartridge comprises multiple fluid reservoirs. This may be implemented in a variety of different ways. For instance the cartridge may have a single container that has multiple fluid reservoirs. Another option is that the cartridge comprises multiple containers with for example one fluid reservoir per container. Another option is that there are multiple containers and that one or more of the multiple containers has more than one fluid reservoir per container. This may be advantageous because the same fluid may be provided to the fluidic structure more than once or a variety of different fluids may be provided enabling more complicated processing of the biological sample into the processed biological sample.

In another embodiment the multiple fluid reservoirs are operable for being opened at different angular positions of the at least one container relative to the cartridge. For example in the case where there is multiple reservoirs on the same container rotating the container to different angular positions may open the different multiple fluid reservoirs independent of each other.

In another embodiment the at least one container has multiple surfaces. Seals for the multiple chamber are distributed on two or more of the multiple surfaces. For instance reservoirs can be located on opposite or different sides of the at least one container.

In another embodiment the first frictional element and the second frictional element comprise any one of the following: a roughened surface, surfaces with adhesive properties, a series of bumps, matching sinusoidal surfaces, a press fit, a breakaway structure, and a ratchet structure. The use of any of these structures or a combination of them have the advantage that they may prevent the container from rotating relative to the cartridge when it is not forced by an actuator. This reduces the possibility that the fluid within a particular fluid reservoir will be dispensed accidentally.

In another embodiment one of the at least one container is a centrally-located container. The rotational axis passes through the centrally-located container.

In another embodiment the cavity of the centrally-located container is cylindrical. The central cavity is cylindrically symmetric about the rotational axis.

In another embodiment one or more of the at least one container is configured for sliding in the cavity. The one or more of the at least one container is configured for rotating about the rotational axis of the cartridge by sliding in the cavity.

For example the container may rotate about a pivot point located on the rotational axis. In the off-centered variant, the container still rotates about the rotational axis of the cartridge; however this motion is now a sliding motion within the cavity, e.g. a sliding motion on a rail-like structure which is located on a segment of a circle around the rotational axis of the cartridge. It is also possible for a centrally located container to be mounted on a rail.

In another embodiment one or more of the at least one container comprises a guiding structure for guiding the sliding motion within the cavity.

In another embodiment the guiding structure is any one of the following: a rail and/or the walls of the cavity.

In another embodiment the cartridge comprises a carrier structure and a cover structure or lid structure which form the cavity. The carrier structure comprises a disc-like portion. The disc-like portion has a circular shape. The circular profile has a center. The rotational axis passes through the center. The fluidic structure may be located within the carrier structure. The cover may be a plastic structure which is thinner than the carrier structure. In some examples the cover may also be disc-like also with the axis going through its center.

In another embodiment the cartridge comprises an opening. The at least one container is operable for being rotationally actuated relative to the cartridge through the opening. The opening exposes the first engaging surface. The first engaging surface and the second engaging surface are connected for mating mechanically. For instance the first engaging surface and the second engaging surface may be a structure which interlock such as a hex shape or a triangular or square shape.

In some examples where the cartridge is within the central cavity the rotational axis may pass through the opening. The opening may for instance be in the cover or the carrier structure.

The engaging surface could for example be a peg, multiple pegs, pins, or a more complex mechanical structure which interlocks.

In another embodiment the opening is sealed with a cover layer.

The cover layer could for instance be removed prior to use. It could also be a thin foil or film which is simply pierced or breaks away when the at least one container is actuated/engaged by the mechanical actuator.

In another embodiment the first engaging surface and the second engaging surface are configured for mating magnetically. For example a particular container may have a magnet or ferromagnetic or other magnetic material attached to it. A magnet may then be used to force the container to rotate about the rotational axis relative to the cartridge without any direct physical contact. The rotational actuator could for instance use a permanent magnet or an electromagnet.

In another embodiment the at least one fluid is any one of the following: a dispersion, a fluid comprising nanoparticles, a fluid comprising a blood grouping reagent, a fluid comprising an immune reagent, a fluid comprising an antibody, a fluid comprising an enzyme, a fluid comprising one or more substrates for an enzymatic reaction, a fluid comprising fluorescence emitting molecules, a fluid comprising molecules for measuring immunochemical reactions, a fluid comprising molecules for measuring reactions of nucleic acids, a fluid comprising a recombinant protein, a fluid comprising virus isolate, a fluid comprising a virus, a fluid comprising a biological reagent, a solvent, a diluent, a buffer, a fluid comprising a protein, a fluid comprising a salt, a detergent, a fluid comprising a fluid comprising a nucleic acid, a fluid comprising an acid, a fluid comprising a base, an aqueous solution, a non-aqueous solution and combinations thereof.

It should be noted that if the cartridge has more than one fluid reservoir then you may have the same fluid multiple times or you can have any combination of different fluids.

In another embodiment the at least one container is multiple containers.

In another embodiment the cartridge is formed from a carrier structure and a cover.

In another embodiment the at least one cavity is formed between the carrier structure and the cover.

In another embodiment the piercing structure is arranged to pierce the pierceable seal perpendicular to the rotational axis.

In another embodiment the cavity has a first planar surface perpendicular to the rotational axis and the container has a second planar surface perpendicular to the rotational axis.

In another embodiment the at least one container is configured to rotate about the rotational axis such that the first planar surface and the second planar surface maintain a constant distance.

In another embodiment the first frictional element is formed on the first planar surface and the second frictional element is formed on the second planar surface.

In another embodiment the first frictional element and the second frictional element are configured to remain in contact when the at least one container is rotated about the rotational axis.

In another embodiment the fluidic structure is formed from the carrier structure and the cover.

In another embodiment the duct is formed from the carrier structure and the cover.

In another embodiment the at least one piercing structure is formed from the carrier structure.

In another embodiment the container is completely within the cover and the carrier structure. For example, the carrier structure may have an outer diameter that is symmetric about the rotational axis. The container may be completely within the outer diameter.

In another embodiment the carrier structure is disk shaped.

In another embodiment the cavity has a first planar surface, and wherein the container has a second planar surface.

In another embodiment the first frictional element is formed on the first planar surface. The second frictional element is formed on the second planar surface. The first frictional element and the second frictional element are configured to remain in contact when the at least one container is rotated about the rotational axis.

In another embodiment, the first planar surface is perpendicular to the rotational axis. The second planar surface is perpendicular to the rotational axis.

In another embodiment, the at least one container is constrained to rotate about the rotational axis such that the first planar surface and the second planar surface maintain a constant distance.

In another embodiment, the piercing structure is arranged to pierce the pierceable seal perpendicular to the rotational axis.

In another embodiment, the at least one container is constrained to enable only rotational motion about the rotational axis of the cartridge within the cavity.

In another embodiment, the at least one container comprises a sidewall, and wherein the sidewall comprises the pierceable seal. The side wall may in some examples be a surface that is parallel to the rotational axis. In another example the side wall may be a curved surface that has at least one point that is parallel to the rotational axis.

In another embodiment, the pierceable seal and the rotational axis form an acute angle.

In another aspect the invention provides for an automatic analyzer configured for receiving a cartridge according to an embodiment. The automatic analyzer comprises a cartridge spinner, a rotational actuator, a measurement system and a controller configured to control the automatic analyzer. The measurement system may for example an optical measurement system or an electrical measurement system.

The cartridge spinner is operable for receiving the cartridge and for spinning the cartridge about the rotational axis. The measurement system is operable for making the measurement using the measurement structure. The controller is configured or programmed with executable instructions to rotate the at least one container relative to the cartridge to open the pierceable seal using the rotational actuator. The controller is further configured or programmed with executable instructions to control the rotational rate of the cartridge to process the biological sample into the processed biological sample using the fluidic structure by controlling the cartridge spinner.

The controller is further configured or programmed with executable instructions to control the rotational rate of the cartridge to force the at least one fluid through the duct and through at least a portion of the fluidic structure. The rotational friction causes the at least one container to rotate at the same rate as the cartridge if the rotational actuator is not in engagement with the container. The controller is further configured or programmed with executable instructions to perform the measurement using the measurement structure and the measurement system. There may be more than one rotational actuator present. For instance if the cartridge has more than one container a particular rotational actuator may be operable for rotating each of the containers relative to the cartridge or there may be more than one rotational actuator for one or more of the containers. In some examples the cartridge may be rotated to different positions relative to the rotational actuator so that the rotational actuator engages a different container.

In another embodiment the automatic analyzer is configured for holding the at least one container in a fixed rotational position relative to the automatic analyzer using the rotational actuator while rotating the cartridge.

In another embodiment the automatic analyzer is configured for rotating the rotational actuator with the cartridge. The rotational actuator is configured for rotating the at least one container relative to the cartridge during rotation of the cartridge.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which.

DETAILED DESCRIPTION

Like numbered elements in these figures are either equivalent elements or perform the same function. Elements which have been discussed previously will not necessarily be discussed in later figures if the function is equivalent.

Figure 1:
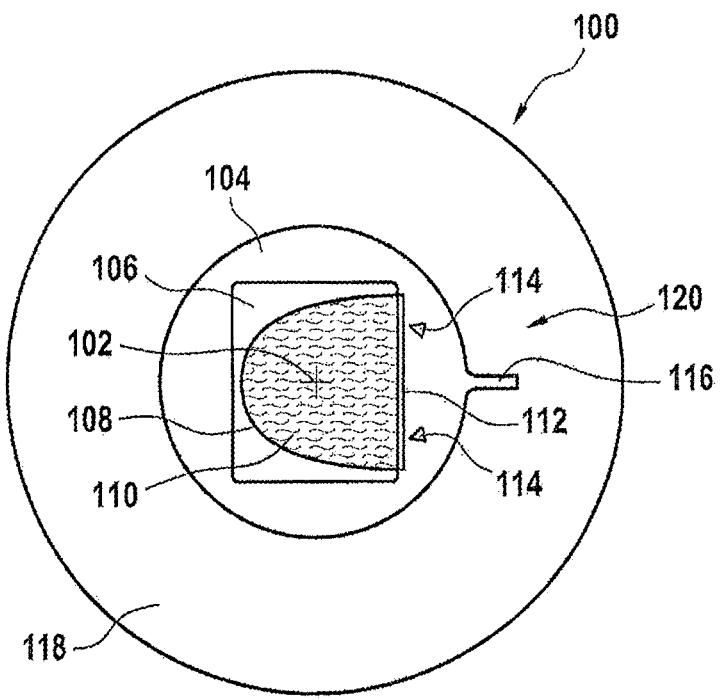
FIG. 1 shows a top view of an example of a cartridge.

FIG. 1 shows a top view of an example of a cartridge 100. Not all components are shown in this cartridge. The cartridge 100 has an axis of rotation or rotational axis 102. The location of the center of the cartridge 100 and the axis of rotation is indicated by the x labeled 102. The cartridge 100 has a central cavity 104. Within the central cavity 104 is a container 106 which has a fluid reservoir 108 that is filled with a fluid 110. One side of the container 106 is sealed with a pierceable seal 112. Within the central cavity 104 are a number of piercing elements 114. The container 106 is operable or configured for pivoting or rotating about the axis of rotation 102. Rotating the container 106 about the axis of rotation 102 causes the pierceable seal 112 to be pressed against a piercing element 114. When this happens the piercing element ruptures or pokes a hole in the pierceable seal 112 and allows the fluid 110 within the fluid reservoir 108 to escape and go into the central cavity 104. There is a duct 116 that connects the central cavity 104 to the body or carrier structure 118 of the cartridge 100. There is a space 120 where a fluidic structure can be placed for processing a biological sample into a processed biological sample such that a measurement can be performed.

Figure 2:
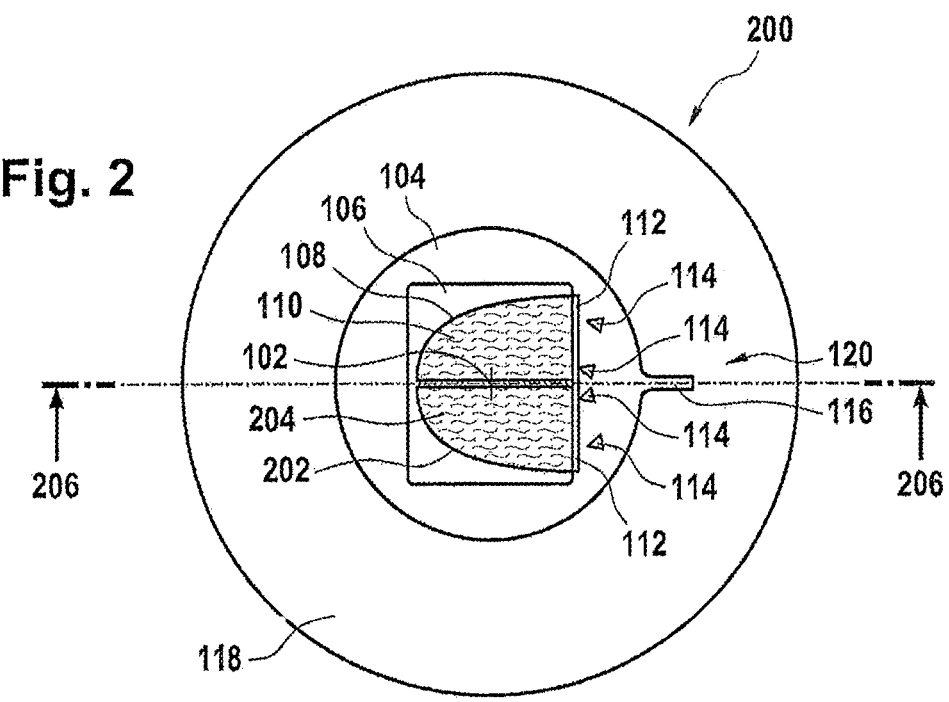
FIG. 2 shows a further example of a cartridge.

FIG. 2 shows a further example of a cartridge 200. The example shown in FIG. 2 is similar to that shown in FIG. 1 except the container 106 has a first fluid reservoir 108 and a second fluid reservoir 202. The first reservoir 108 is filled with a fluid 110 and the second reservoir 202 is filled with a second fluid 204. In some cases the fluid 110 and 204 are the same fluid; in other cases they are different. In this example there is a pierceable seal 112 sealing each of the fluid reservoirs 108, 202 independently. By rotating the container 106 clockwise the piercing elements 114 open the first fluid reservoir 108. By rotating the container 106 counterclockwise the second fluid reservoir 202 is opened. In both the examples shown in FIG. 1 and FIG. 2 the cartridge 100, 200 can be rotated at relatively high rates about the axis of rotation 102 and this will drive the fluid 110 or 204 through the duct 116. The dashed line 206 in FIG. 2 shows the location of a cross-sectional view in FIG. 4.

Figure 3:
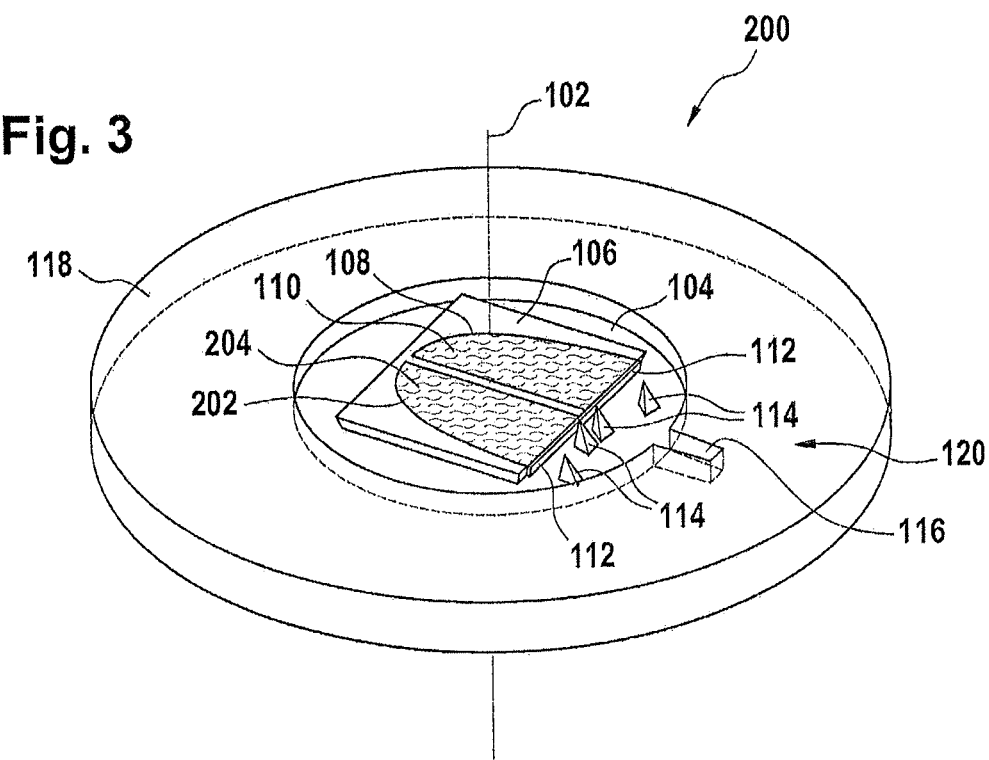
FIG. 3 shows a perspective view of the cartridge of FIG. 2.

FIG. 3 shows a perspective view of the same cartridge 200.

Figure 4:
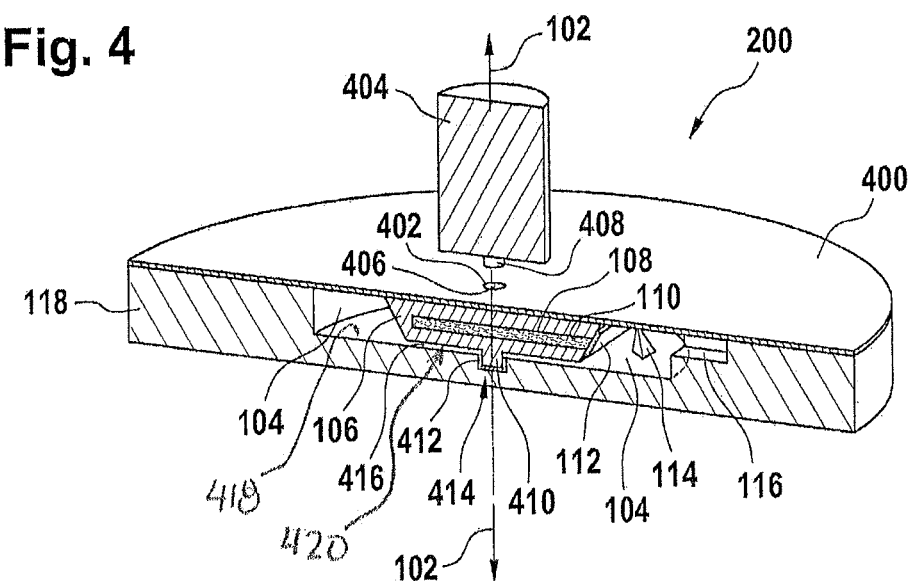
FIG. 4 shows a perspective cross-sectional view of the cartridge 200 of FIG. 2.
Figure 5:
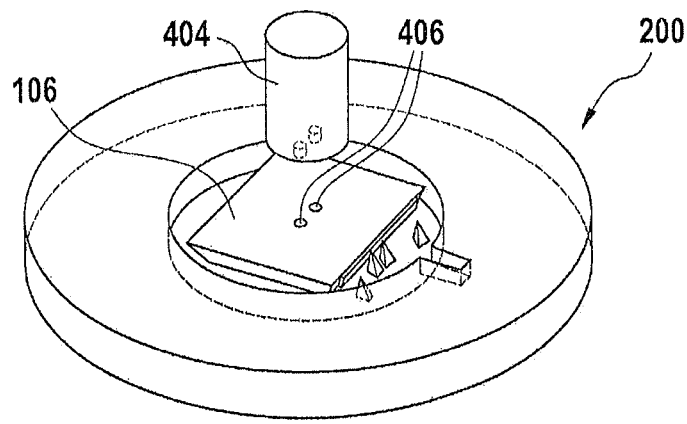
FIG. 5 illustrates part of a method of using the cartridge of FIG. 2.

FIG. 4 shows a perspective cross-sectional view of the cartridge 200 of FIG. 2. FIG. 4 shows a cross-sectional view along the line 206. The cartridge 200 can be seen as being made up of a carrier structure 118 and a cover 400. In this example there is a hole 402 in the cover 400 for a rotational actuator 404 to engage the container 106. The container 106 has a first engaging surface 406 and the rotational actuator 404 has a second engaging surface 408. In this example the second engaging surface 408 is a pin-like structure which digs into the cartridge and contacts the container 106. In some examples the hole 402 may be larger, in some examples it may be covered with a seal that may be removed by an operator before use. In other examples a seal may cover the hole 402 and then the second engaging surface 408 pushes through the seal and contacts the container 106.

The container 106 has a small shaft 410 that extends a short way into the carrier structure 118. This may be used as a first frictional element 412 that contacts a second frictional element 414 of the carrier structure 118. For instance the shaft 410 may have a press fit or may have some material or surface which makes friction when the container 106 tries to rotate about the axis 102. Alternatively or in addition to the space 416 between the container 106 and the carrier structure 118 may have a structure which is used to increase the rotational friction of the container 106. For instance small bits of these surfaces may be roughened or have a structure which hinders the free rotation of the container 106 relative to the cartridge 200.

The carrier structure 118 can be seen as having a first planar surface 418 that is formed in the cavity 104. The surface is perpendicular to the rotational axis 102. The container 106 can be seen as having a second planar surface 420 that is perpendicular to the rotational axis 102.

As an alternative, it is also possible to have surfaces that are not perpendicular to the rotational axis. For example frictional elements may be caused by surfaces that are parallel or cylindrically symmetric about the rotational axis. In some examples the container may have side walls or other surfaces that can contact the cavity. The container may also be supported by a bearing or bushing that also functions as a frictional element.

The geometries of the surfaces forming frictional elements may also vary. The geometries of such surfaces may comprise both perpendicular and parallel components (e.g. 45° surfaces or concave/convex surfaces can be used).

FIGS. 5-11 illustrate a method of using the cartridge 200. First in FIG. 5 a starting position is shown. The cartridge 200 and the container 106 are in a starting position. The rotational actuator 404 is withdrawn and is not touching the cartridge 200. If the cartridge 200 is rotated the container 106 will rotate with the disc at the same rate.

Figure 6:
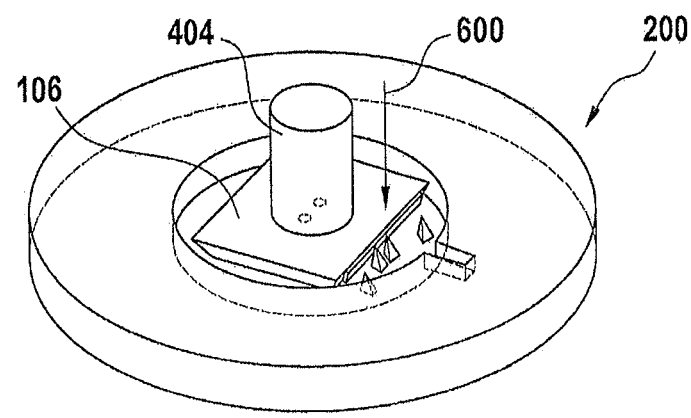
FIG. 6 further illustrates part of a method of using the cartridge of FIG. 2.

Next in FIG. 6 the rotational actuator 404 has been moved forward in the direction 600 such that the rotational actuator 404, the surfaces 406 and 408 mate with each other. In this particular example this fixes the position of the container 106 relative to the rotational actuator 404.

Figure 7:
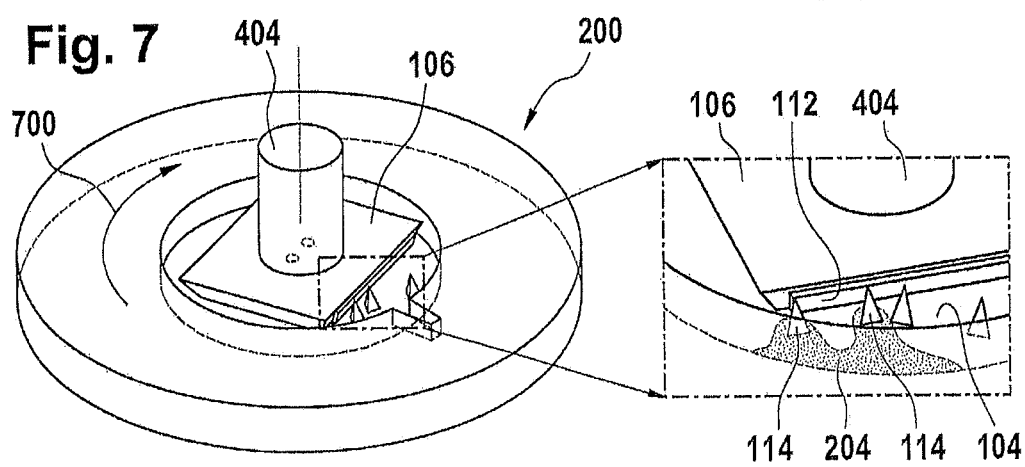
FIG. 7 further illustrates part of the method of using the cartridge of FIG. 2.

Next in FIG. 7 the rotational actuator 404 holds the container 106 in a fixed location and the cartridge 200 is rotated clockwise along the rotation 700. This causes the piercing elements 114 to pierce the seal 112 of the fluid reservoir 202. This causes the fluid 204 to leak out and drain into the central cavity 104.

Figure 8:
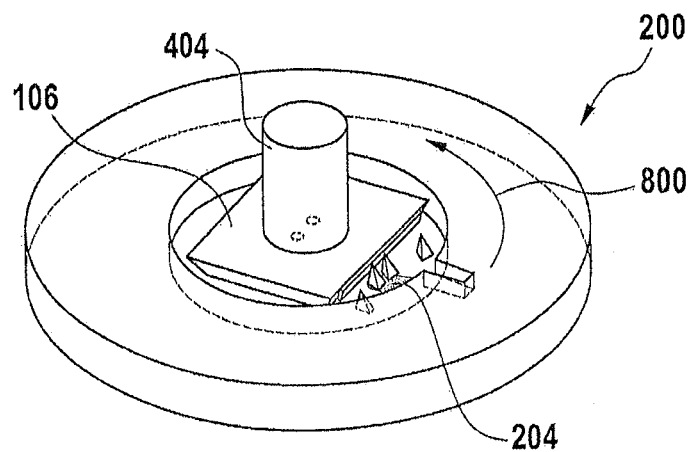
FIG. 8 further illustrates part of the method of using the cartridge of FIG. 2.

Next in FIG. 8 the cartridge 200 is rotated back in a counterclockwise direction 800 to put the position of the container 106 relative to the rest of the cartridge 200 back into its original starting position.

Figure 9:
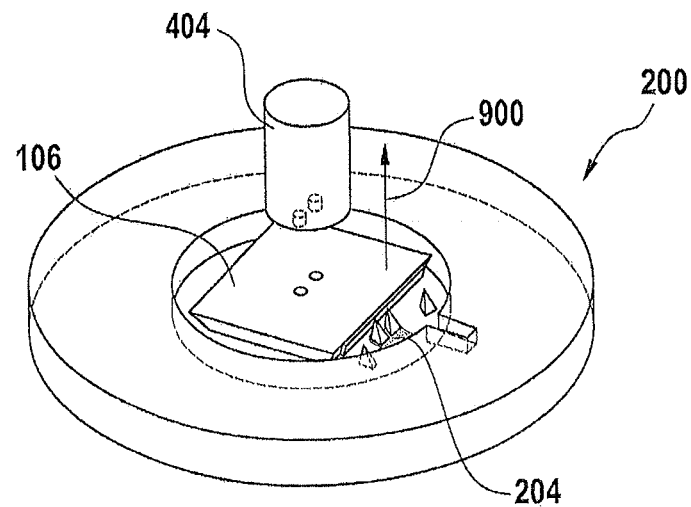
FIG. 9 further illustrates part of the method of using the cartridge of FIG. 2.

Next in FIG. 9 the rotational actuator 404 is withdrawn from the cartridge in the direction 900. As the rotational actuator 404 has moved away from the container the container 106 is no longer in a fixed location. A further rotation of the cartridge 200 will cause a rotation of the container 106 as well.

Figure 10:
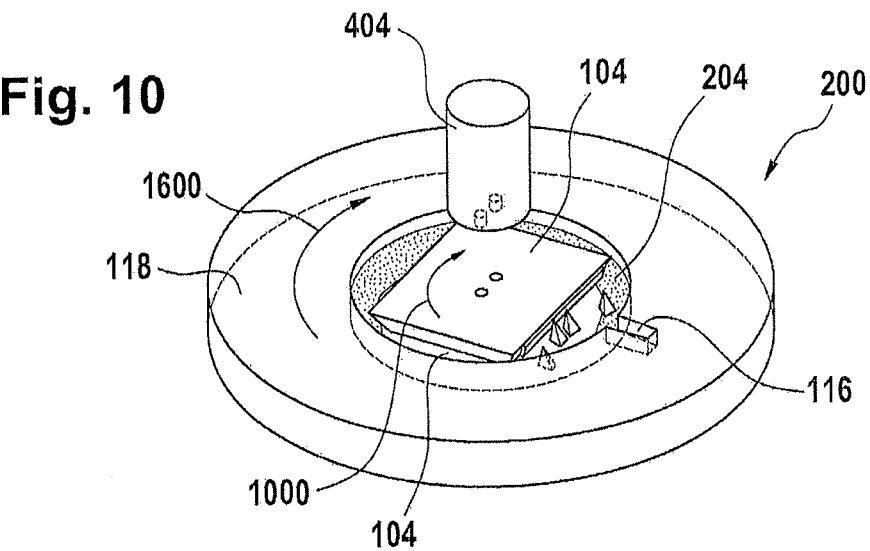
FIG. 10 further illustrates part of the method of using the cartridge of FIG. 2.

Next in FIG. 10 the rotational actuator 404 has been withdrawn. Then the cartridge 200 is rotated and the carrier structure 118 and the container 106 rotate together at the same rate. Arrows 1000 show the direction of rotation. This rotation forces the fluid 204 out of the pierced fluid reservoir 204 and into the central cavity 104. Further rotation forces the fluid 204 through the duct 116 into the fluidic structure of the cartridge 200.

Figure 11:
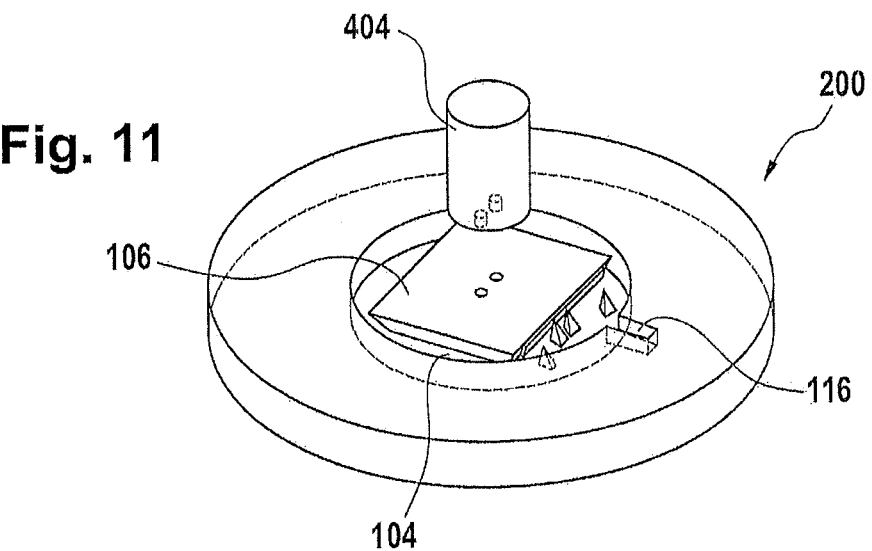
FIG. 11 further illustrates part of the method of using the cartridge of FIG. 2.

FIG. 11 shows the cartridge 200 where the fluid reservoir 204 and the central cavity 104 have both been emptied of fluid, it has all gone through the duct 116 into the fluidic structure of the cartridge 200.

Figure 12:
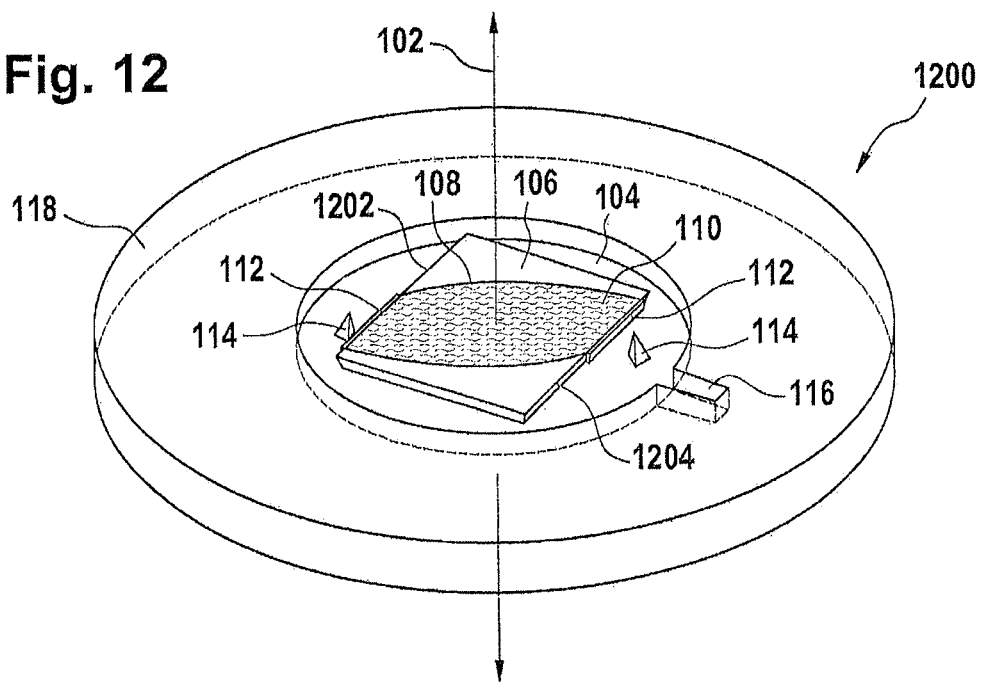
FIG. 12 shows an alternative design of a cartridge.

FIG. 12 shows an alternative design of a cartridge 1200. The design of the cartridge 1200 is similar to the design of the cartridge 100 shown in FIG. 1, however in this example the container 106 has a pierceable seal 112 on opposite ends from each other located on surfaces 1202 and 1204. There is a piercing element 114 located near each pierceable seal 112. This particular design may have the advantage that the fluid reservoir 108 is opened at two ends. This may lead to better venting of the fluid reservoir 108 and/or faster draining of the fluid reservoir 108.

Figure 13:
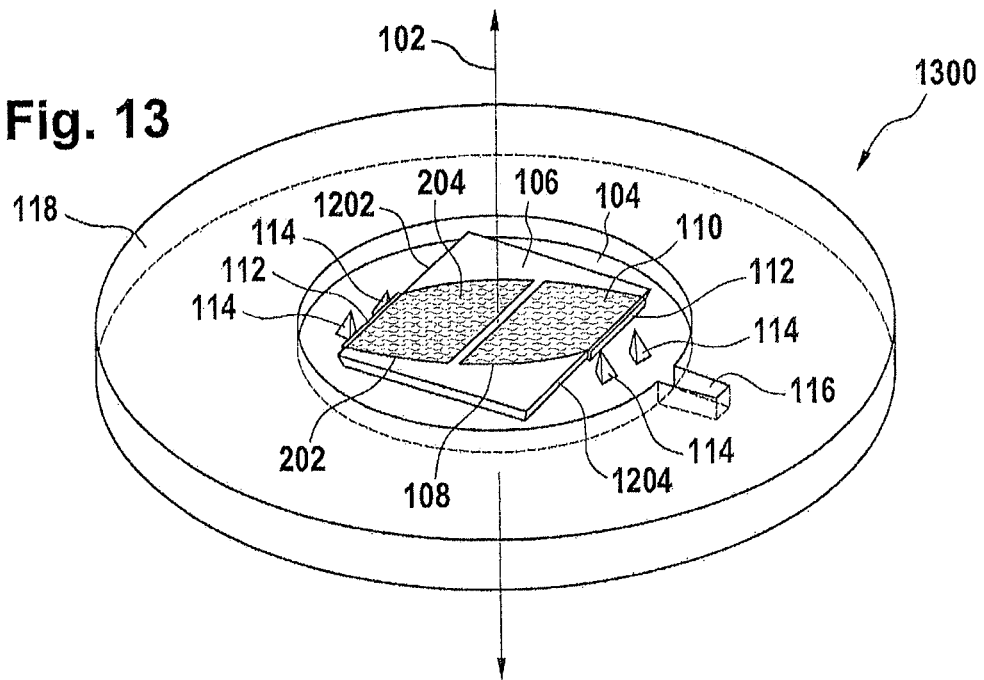
FIG. 13 shows an alternative design of a cartridge which is similar to the cartridge of FIG. 2.

FIG. 13 shows a cartridge 1300 similar to the cartridge 200 shown in FIG. 2. However, in this example there are pierceable seals 112 on opposite ends of the sides of the container 106 on opposing surfaces 1202 and 1204. Rotating the container 106 clockwise about the axis 102 relative to the carrier structure 118 causes the pierceable seal 112 of both the first fluid reservoir 108 and the second fluid reservoir 202 to be pierced at the same time. This may have the advantage that the first fluid 110 and the second fluid 204 can be mixed in the central cavity 104. Alternatively, the reservoirs may be opened one after the other causing one fluid to released first and the second fluid to be released in a subsequent step.

Figure 14:
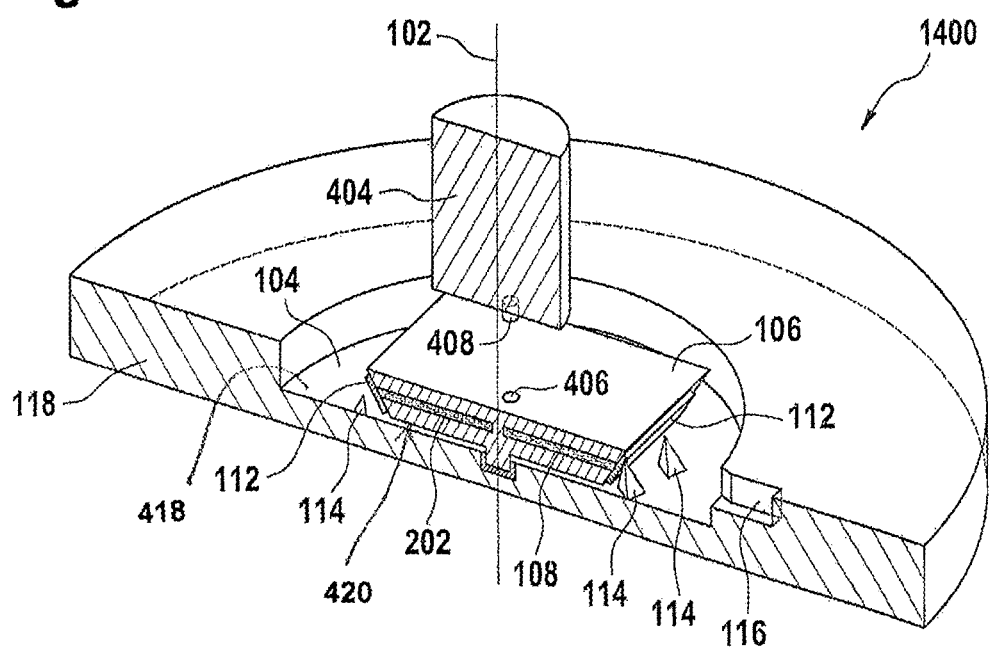
FIG. 14 shows a cross-sectional view of the cartridge of FIG. 13.

FIG. 14 shows a cross-sectional view of the cartridge 1300 shown in FIG. 13. This view is similar to the view before of cartridge 200.

Figure 15:
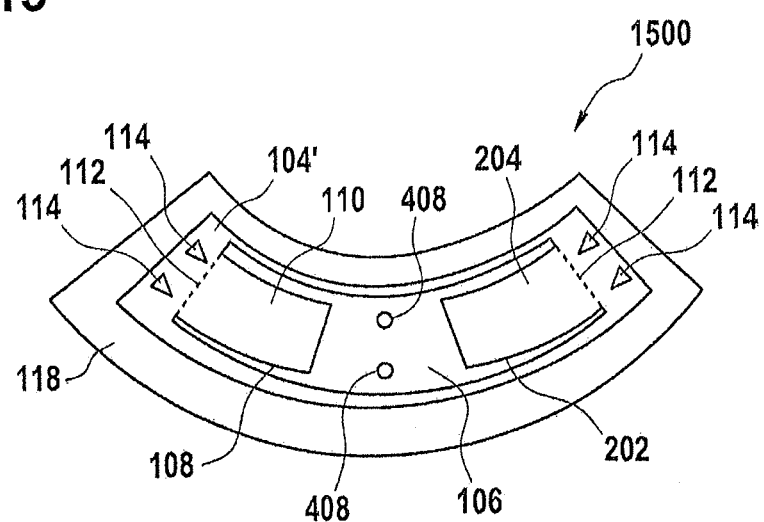
FIG. 15 shows a portion of a cartridge with a the container that is off the rotational axis.

FIG. 15 shows a portion of a cartridge 1500. In this example only a small section of the carrier structure with a cavity 104' is shown. In this example the cavity 104' is off of the axis of rotation 102. The container 106 is designed to slide within the cavity 104' but however rotate around the axis of rotation 102. In this example the container 106 can be rotated either clockwise or counterclockwise around the axis of rotation 102. There are two different fluid reservoirs 108, 202 that can be independently opened.

Figure 16:
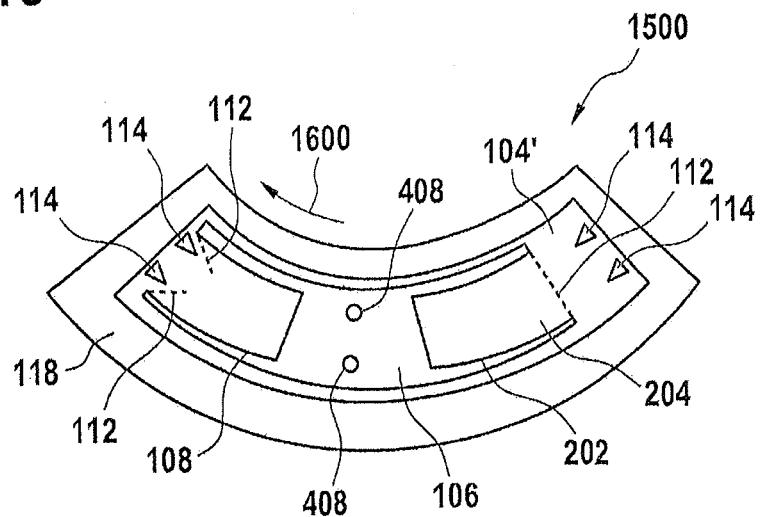
FIG. 16 illustrates the movement of the container with the cartridge of FIG. 15.

In FIG. 16 the same portion 1500 of a cartridge showing the cavity 104' is shown again. In this case the container 106 has been rotated clockwise relative to the cartridge 1500 around the axis of rotation 102 along the rotational direction 1600. The first fluid reservoir 108 has been opened because the piercing elements 114 have opened the pierceable seal 112.

Figure 17:
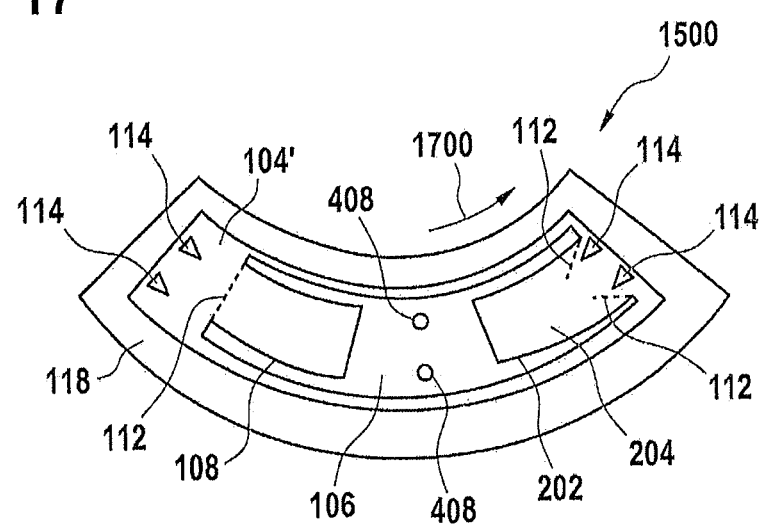
FIG. 17 further illustrates the movement of the container with the cartridge of FIG. 15

FIG. 17 is similar to FIG. 16 except the container 106 has been rotated counterclockwise relative to the cartridge 1500 in the direction 1700 about the axis of rotation 102. In this example the second fluid reservoir 202 has been opened instead.

Figure 18:
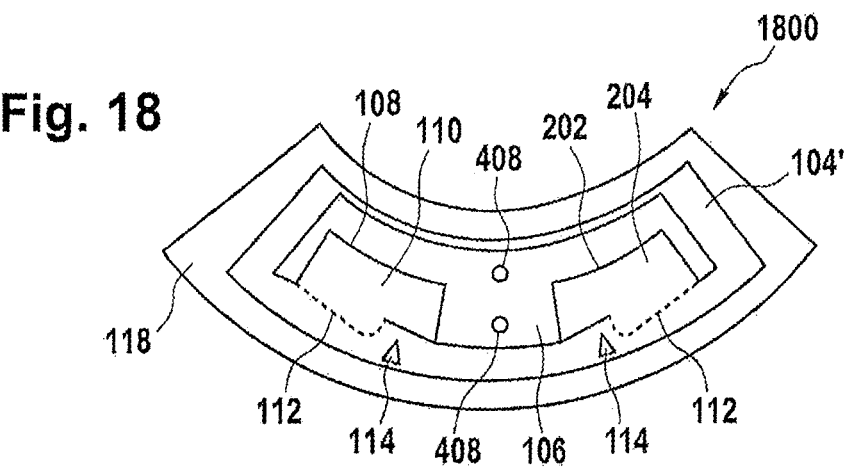
FIG. 18 shows an alternative portion of a cartridge with a container that is off the rotational axis.

FIG. 18 shows a portion of a cartridge 1800 showing the cavity 104'. The example shown in FIG. 18 is similar to that shown in FIG. 15 except the design of the container 106 is different. In this example the pierceable seals 112 extend below the container 106. As the container 106 is rotated about the rotational axis relative to the cartridge 1800 the pierceable seals 112 are pierced or torn by the piercing elements 114.

Figure 19:
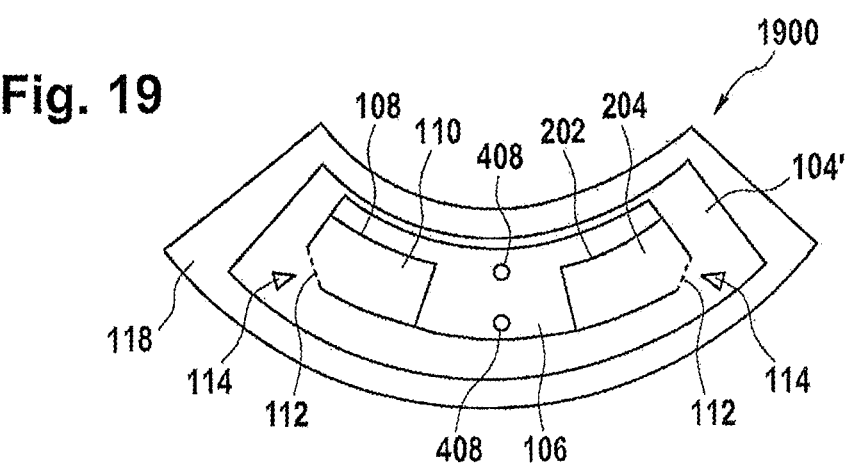
FIG. 19 shows a further example of a portion of a cartridge with a container that is off the rotational axis.

FIG. 19 shows a further example of a portion of a cartridge 1900 showing cavity 104'. The example shown in FIG. 19 is similar to that shown in FIG. 15 except the pierceable seals 112 are on the corners of the container 106 instead of at the ends. The fluid reservoirs 108, 202 will still be opened by the rotation of the container 106 relative to the cartridge 1900 about the rotational axis.

Figure 20:
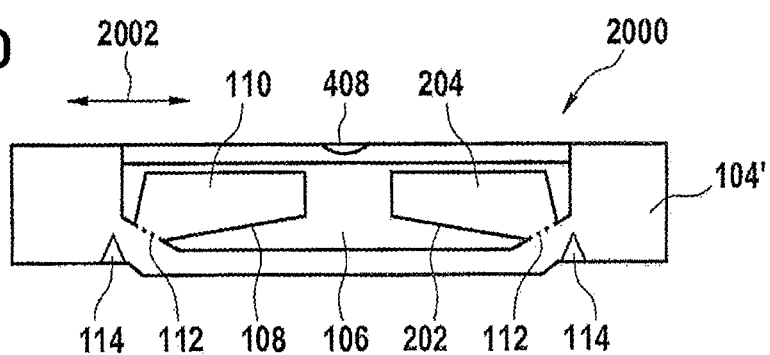
FIG. 20 shows an example of a cartridge with a container 106 that is off the rotational axis.

FIG. 20 shows a different example of a cartridge with a container 106 that is off axis. FIG. 20 shows a portion of a cartridge 2000 showing the cavity 104'. This is a cross-sectional view instead of a top view such as is shown in FIGS. 15-19. The container 106 can be rotated about the rotational axis and centrally moved relative to the cartridge 2000 in either of the directions labeled 2002. Moving the cartridge in either direction 2002 causes the piercing elements 114 to tear open the pierceable seals 112.

Figure 21:
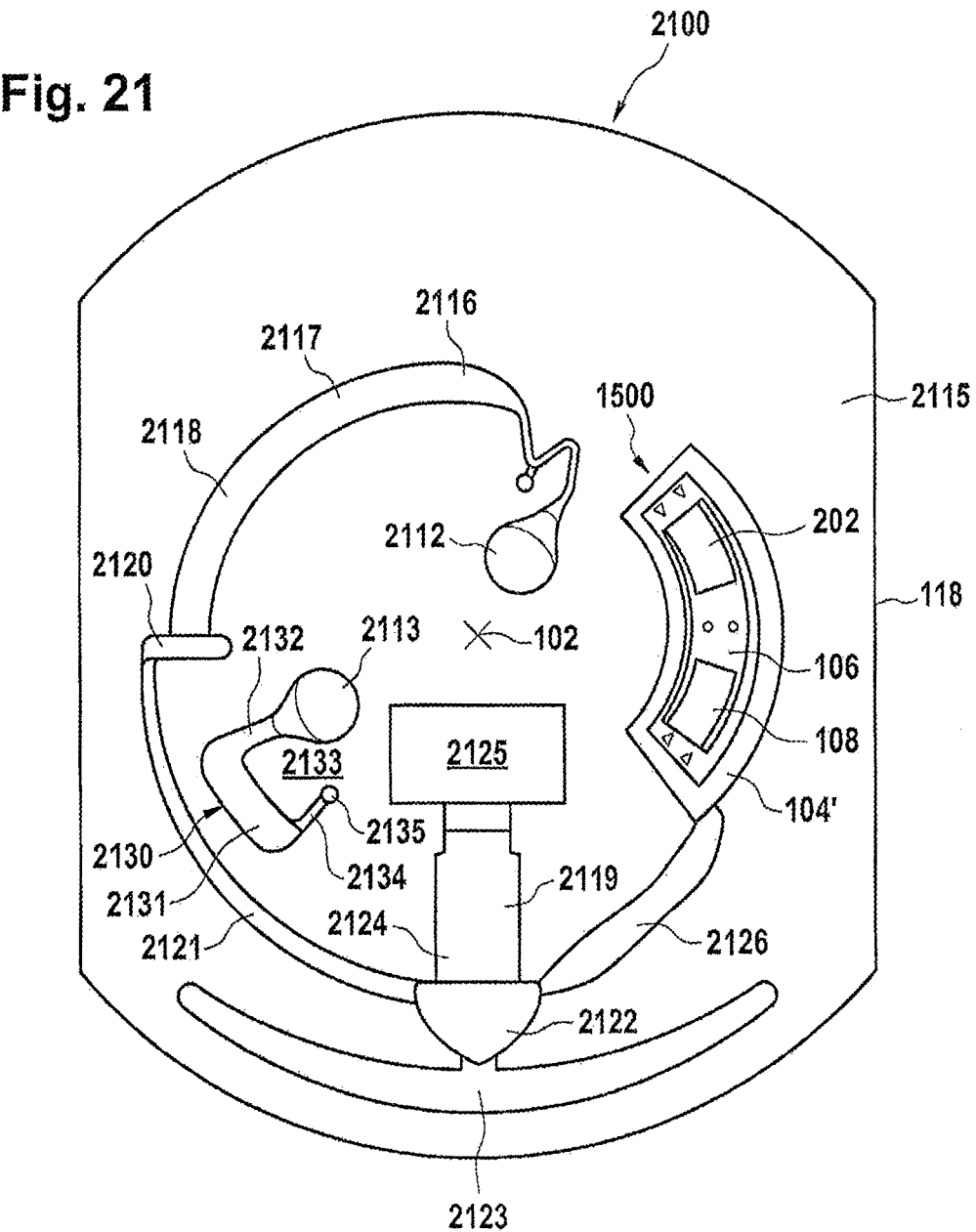
FIG. 21 shows an example of a cartridge which incorporates the container and cavity of FIG. 15.

FIG. 21 shows an example of a cartridge 2100 which incorporates the container 106 and cavity 104' structure 1500 that is illustrated in FIG. 15.

FIG. 21 shows a schematic view of two embodiments of the cartridge 2100 or test element. The test element 2100 comprises a housing 2115 having a substrate or carrier structure 118. In addition to the substrate 118, the disc-shaped test element 2100 also typically contains a cover layer, which is not shown for the sake of clarity. The cover layer can fundamentally also carry fluidic structures, however, it will typically only have openings for delivering liquids or vent openings. A central hole or a shaft can be provided, around which the test element rotates. The rotation axis 102 in one embodiment is positioned inside the test element, or in another embodiment outside the test element.

The housing 2115 of the test element 2100 has fluidic or micro fluidic as well as chromatographic structures. The sample liquid, in particular whole blood, is delivered to the test element 2100 via the sample supply opening 2112. A sample analysis channel 2116 comprises the sample supply opening 2112 at its beginning and a measuring zone 2119 at its end in the flow direction. A channel section 2117, through which a liquid sample flows in the predefined flow direction to the measuring zone 2119, extends between the sample supply opening 2112 and the measuring zone 2119. The liquid transport in the test element 2100 occurs by capillary forces and/or centrifugal forces.

The flowing and/or the flow velocity of the liquid sample can be influenced by suitable selection of the fluidic structures of the sample analysis channel 2116. For example, in one embodiment the dimensions of the channel sections 2117, 2118, 2121 is selected in such a manner that the occurrence of capillary forces is encouraged. In other embodiments, the surfaces of the channel sections is hydrophilized. The further flowing or filling of the individual channel sections of the sample analysis channel 2116 can also only be made possible after the action of an external force, for example, in one embodiment a centrifugal force.

In still other embodiments, the different sections of the sample analysis channel 2116 are dimensioned differently and/or provided for different functions. For example, in one embodiment a primary channel section 2118 can contain a reagent system reacting with the body fluid sample, of which at least one reagent in one embodiment is provided in dried or lyophilized form. It is also possible in another embodiment that at least one reagent is provided in liquid form, which is supplied to the test element 2100 by the fluid reservoirs 108 or 202 of the container 106.

The channel section 2117 comprises a primary channel section 2118, a capillary stop 2120, and a secondary channel section 2 21. In one embodiment, the capillary stop 2120 is implemented as a geometric valve or in another embodiment as a hydrophobic barrier. The secondary channel section 2121 adjoining the capillary stop 2120 guides a sample quantity measured off by the capillary stop 2120. The quantity flowing through the capillary stop 2120 is controlled by centrifugal forces using the rotational velocity of the test element 2100.

At suitable rotational velocities, the separation of red blood cells or other cellular sample components is started in the secondary channel section 2121. The reagents may be contained in a reagent system present in channel section 2118, which may be provided in dried form in one embodiment, are already dissolved upon entry of the sample liquid into the secondary channel section 2121. Components of the sample-reagent mixture are captured in the collection zones 2122 (plasma collection zone) and 2123 (erythrocyte collection zone), which are implemented as chambers.

The measuring zone or measurement structure 2119 adjoining the collection zone 2122 in one embodiment includes a measuring chamber 2124, which in one embodiment contains a porous, absorbent matrix. A waste chamber 2125 is positioned after the measuring chamber 2124 in the flow direction. In one embodiment, the reaction participants, sample components, and/or reagent components is disposed of in the waste chamber 2125 after flowing through the measuring chamber 2124.

The waste chamber 2125 in one embodiment has a fluid connection to the measuring zone 2119 in such a manner that it receives the liquid which has flowed through the measuring zone 2119.

In addition, a washing solution supply is provided by the container 106. A washing solution channel or duct 2126 adjoins to cavity 104' The washing solution channel 2126 in one embodiment is in fluid communication with the measuring zone 2119 at its end such that a washing solution is suctioned through the washing solution channel 2126 into the measuring chamber 2124. The matrix of the measuring chamber 2124 is washed and any excess, interfering reaction participants are removed. The washing solution subsequently also reaches the waste chamber 2125.

Figure 22:
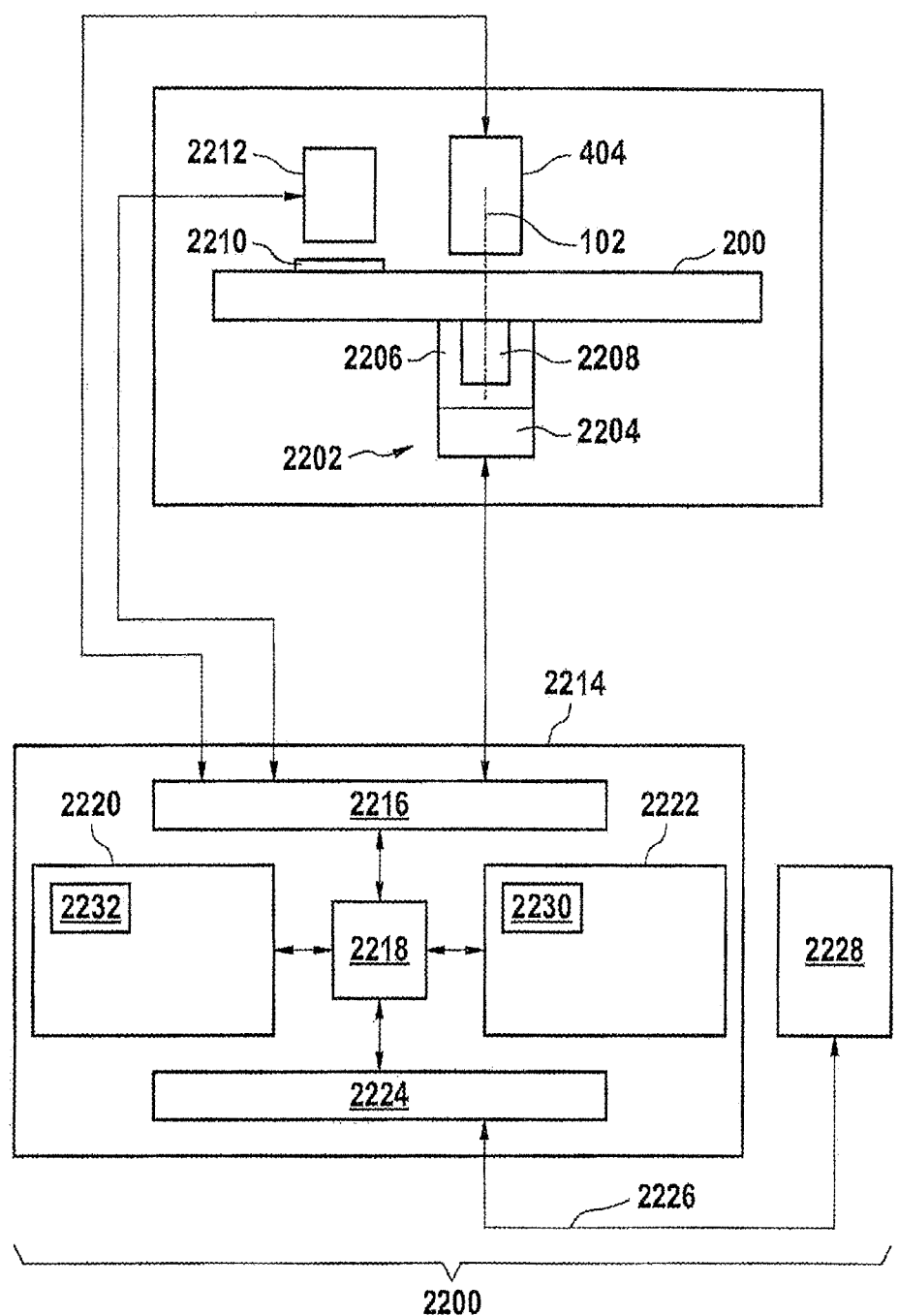
FIG. 22 shows an example of an automatic analyzer.

FIG. 22 shows an example of an automatic analyzer. The automatic analyzer 2200 is adapted for receiving a cartridge 200. There is a cartridge spinner 2202 which is operable for rotating the cartridge 200 about the rotational axis 102. The cartridge spinner 2202 has a motor 2204 attached to a gripper 2206 which attaches to a portion of the cartridge 2208. The cartridge 200 is shown further as having a measurement or transparent structure 2210. The cartridge 200 can be rotated such that the measurement structure 2210 goes in front of a measurement system 2212 which can perform for example an optical measurement on the processed biological sample. The rotational actuator 404 as was shown previously is also shown in this FIG. It can be used to open one or more fluid reservoirs in the cartridge 200. The actuator 404, the cartridge spinner 2202, and the measurement system 2212 are shown as all being connected to a hardware interface 2216 of a controller 2214. The controller 2214 contains a processor 2218 in communication with the hardware interface 2216, electronic storage 2220, electronic memory 2222, and a network interface 2224. The electronic memory 2222 has a machine executable instructions 2230 which enable the processor 2218 to control the operation and function of the automatic analyzer 2200. The electronic storage 2220 is shown as containing a measurement 2232 that was acquired when instructions 2230 were executed by the processor 2218. The network interface 2224 enables the processor 2218 to send the measurement 2232 via network interface 2226 to a laboratory information system 2228.

Figure 23:
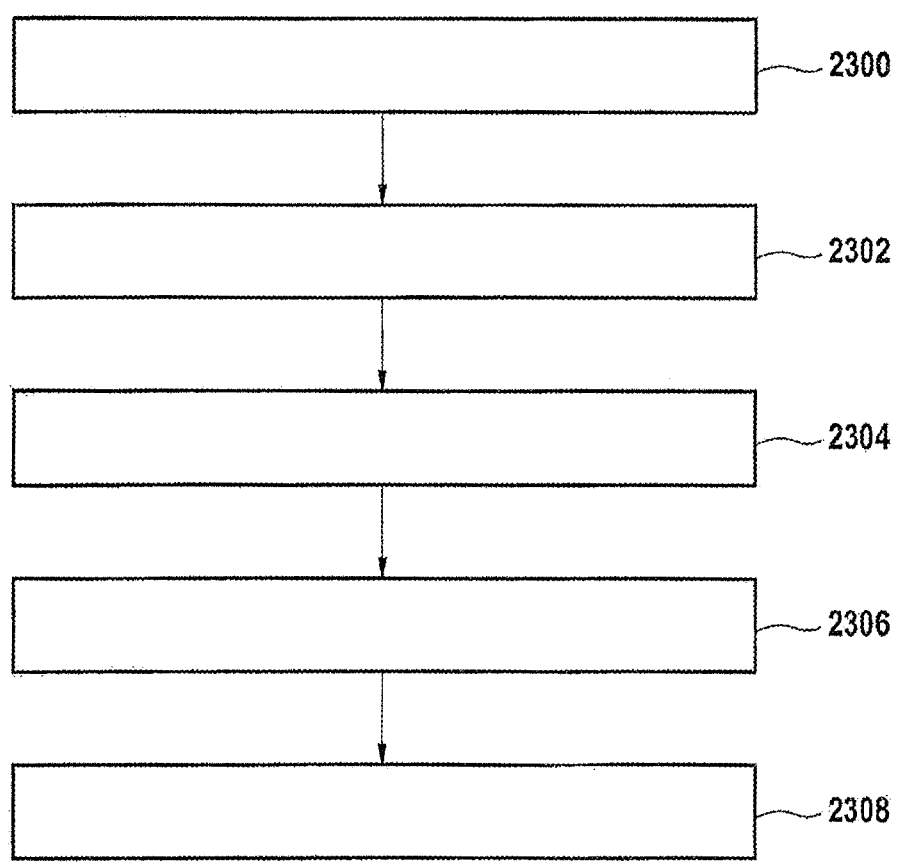
FIG. 23 shows a flowchart which illustrates a method of operating the automatic analyzer of FIG. 22.

FIG. 23 shows a flowchart which illustrates a method of operating the automatic analyzer 2200 of FIG. 22. First in step 2300 a biological sample is placed into a fluidic structure of the cartridge 200. This may be done manually or it may also be done if there is an automatic system for dispensing or pipetting the biological sample into the cartridge 200. Next in step 2302 a torque is applied to the at least one container using the rotational actuator 404 to overcome the friction between the cavity and the at least one container and rotate the at least one container relative the cartridge around the rotational axis 102 of the cartridge 200 to open the pierceable seal. The rotation of the at least one container relative to the cartridge causes the at least one piercing structure to open the seal by piercing the pierceable seal. For instance in the example shown in FIG. 22 the actuator 404 is separate from the motor assembly 2202. The actuator 404 can be used to hold the container stationary while the motor 2204 rotates the cartridge 200. Next in step 2304 the processor 2218 controls the rotational rate of the cartridge to process the biological sample into the processed biological sample using the fluidic structure. Next in step 2306 the processor controls the rotational rate of the cartridge to force the at least one fluid through the duct and through at least a portion of the fluidic structure. The friction between the cavity and the at least one container causes the at least one container to rotate around the rotational axis at the same rate as the cartridge. Finally in step 2308 the measurement 2232 is performed using the measurement structure 2210 using the measurement system 2212. The steps 2302, 2304, 2306 may be performed multiple times and in different orders.

LIST OF REFERENCE NUMERALS 100 cartridge
102 axis of rotation
104 central cavity
104' cavity
106 container
108 fluid reservoir
110 fluid
112 pierceable seal
114 piercing element
116 duct
118 carrier structure
120 space for fluidic structure
200 cartridge
202 second fluid reservoir
204 second fluid
206 cross section line
400 cover
402 opening
404 rotation actuator
406 first engaging surface
408 second engaging surface
410 shaft
412 first frictional element
414 second frictional element
416 space between container and carrier structure
418 first planar surface
420 second planar surface
600 direction
700 clockwise rotation
800 counter clockwise rotation
900 direction
1000 direction of rotation
1200 cartridge
1202 surface of container
1204 surface of container
1300 cartridge
1500 portion of cartridge showing cavity 104'
1600 counter clockwise rotation
1800 portion of cartridge showing cavity 104'
1900 portion of cartridge showing cavity 104'
2000 portion of cartridge showing cavity 104'
2002 rotational direction
2113 flushing liquid supply opening
2115 housing
2116 sample analysis channel
2117 channel section
2118 primary channel section
2119 measuring zone or measurement structure
2120 capillary stop
2121 secondary channel section
2122 plasma collection zone
2123 erythrocyte collection zone
2124 measuring chamber
2125 waste chamber
2130 priming structure
2131 flushing liquid collection chamber
2132 flushing liquid channel
2133 valve
2134 ventilation channel
2135 ventilation opening
2200 automatic analyzer
2202 cartridge spinner
2204 motor
2206 gripper
2208 portion of cartridge
2210 measurement structure
2212 measurement system
2214 controller
2216 hardware interface
2218 processor
2220 electronic storage
2222 electronic memory
2224 network interface
2226 network connection
2228 laboratory information system
2230 executable instructions
2232 measurement
2300 placing the biological sample into the fluidic structure
2302 applying the torque to the at least one container using the rotational actuator to overcome the friction between the cavity and the at least one container and rotate the at least one container relative to the cartridge around the rotational axis of the cartridge to open the pierceable seal
2304 controlling the rotational rate of the cartridge to process the biological sample into the processed biological sample using the fluidic structure
2306 controlling the rotational rate of the cartridge to force the at least one fluid through the duct and through at least a portion of the fluidic structure
2308 performing the measurement through the measurement structure using a measurement system

What is claimed is:

1. A method of performing a measurement of a processed biological sample using a cartridge that is operable for being spun around a rotational axis, the cartridge comprising a carrier structure, a cover provided to the carrier structure, at least one container with at least one fluid reservoir for containing at least one fluid, and a cavity for each of the at least one cartridge, wherein the cavity is formed from the carrier structure and the cover, the at least one container is configured to rotate about the rotational axis of the cartridge within the cavity and relative to the carrier structure, each of the at least one fluid reservoir comprises a pierceable seal, at least one piercing structure for each of the at least one fluid reservoir provided within the cavity, the at least one piercing structure is configured to open the pierceable seal by piercing the pierceable seal upon rotation of the at least one container relative to the carrier structure, the at least one container comprises a first frictional element, a second frictional element is provided within the cavity, the first frictional element mates with the second frictional element to cause friction for the at least one container within the cavity, the at least one container comprises a first engaging surface that is operable to mate with a second engaging surface of a rotational actuator that is operable to apply torque to the at least one container, the cartridge comprises a fluidic structure for processing a biological sample into the processed biological sample, the fluidic structure is formed from the carrier structure and the cover and is located within the carrier structure, the cartridge comprises a duct between the cavity and the fluidic structure, the duct is formed within the carrier structure and the cover, the fluidic structure comprises a measurement structure for enabling the measurement of the processed biological sample, and the fluidic structure is configured to receive the biological sample, the method comprising:

placing the biological sample into the fluidic structure;

applying torque to the at least one container using the rotational actuator to overcome the friction between the first frictional element and the second frictional element within the cavity and rotate the at least one container relative to the carrier structure around the rotational axis of the cartridge to open the pierceable seal, wherein rotating the at least one container relative to the carrier structure causes the at least one piercing structure to open the seal by piercing the pierceable seal;

controlling the rotational rate of the cartridge to process the biological sample into the processed biological sample using the fluidic structure;

controlling the rotational rate of the cartridge to force the at least one fluid through the duct and through at least a portion of the fluidic structure, wherein the friction between the first frictional element and the second frictional element causes the at least one container to rotate around the rotational axis of the axis at the same rate as the carrier structure; and performing the measurement through the measurement structure using a measurement system.

2. A cartridge for an automatic analyzer that is operable for being spun around a rotational axis, the cartridge comprising:

a carrier structure;

a cover provided to the carrier structure;

at least one container with at least one fluid reservoir for containing at least one fluid; and a cavity for each of the at least one cartridge, wherein: the cavity is formed from the carrier structure and the cover, the at least one container is configured to rotate about the rotational axis of the cartridge within the cavity and relative to the carrier structure, each of the at least one fluid reservoir comprises a pierceable seal, at least one piercing structure for each of the at least one fluid reservoir provided within the cavity, the at least one piercing structure is configured to open the pierceable seal by piercing the pierceable seal upon rotation of the at least one container relative to the carrier structure, the at least one container comprises a first frictional element, a second frictional element is provided within the cavity, the first frictional element mates with the second frictional element to cause friction for the at least one container within the cavity, the at least one container comprises a first engaging surface that is operable to mate with a second engaging surface of a rotational actuator that is operable to apply torque to the at least one container, the cartridge comprises a fluidic structure for processing a biological sample into a processed biological sample, the fluidic structure is formed from the carrier structure and the cover and is located within the carrier structure, the cartridge comprises a duct between the cavity and the fluidic structure, the duct is formed within the carrier structure and the cover, the fluidic structure comprises a measurement structure for enabling the measurement of the processed biological sample, and the fluidic structure is configured to receive the biological sample.

3. The cartridge of claim 2, wherein the cartridge comprises multiple fluid reservoirs.

4. The cartridge of claim 3, wherein the multiple fluid reservoirs are operable for being opened at different angular positions of the at least one container relative to the cartridge.

5. The chamber of claim 3, wherein the at least one container has multiple surfaces wherein the pierceable seals for each of the multiple fluid reservoirs are distributed on two or more of the multiple surfaces.

6. The cartridge of claim 2, wherein the first frictional element and the second frictional element comprise any one of the following: roughened surfaces, surfaces with adhesive properties, a series of bumps, matching sinusoidal surfaces, a press fit, a breakaway structure, and a ratchet structure.

7. The cartridge of claim 2, wherein one of the at least one container is a centrally located container, wherein the rotational axis passes through the centrally located container.

8. The cartridge of claim 2, wherein one or more of the at least one container is configured for sliding in the cavity, wherein the one or more of the at least one container is configured for rotating about the rotational axis of the cartridge by sliding in the cavity.

9. The cartridge of claim 2, wherein the carrier structure comprises a disk like portion, wherein the disk like portion has a circular profile, wherein the circular profile has a center, and wherein the rotational axis passes through the center.

10. The cartridge of claim 9, wherein the cartridge comprises an opening, wherein the at least one container is operable for being rotationally actuated relative to the cartridge through the opening, wherein the opening exposes the first engaging surface, wherein the first engaging surface and the second engaging surface are configured for mating mechanically.

11. The cartridge of claim 10, wherein the opening is sealed with a cover layer.

12. The cartridge of claim 2, wherein the first engaging surface and the second engaging surface are configured for mating magnetically.

13. The cartridge of claim 2, wherein the at least one container is multiple containers.

14. The cartridge of claim 2, wherein the measurement structure is a transparent structure and/or comprises two or more electrodes.

15. The cartridge of claim 2, wherein the at least one piercing structure is formed from the carrier structure.

16. The cartridge of claim 2, wherein the at least one container is completely within the cover and the carrier structure.

17. The cartridge of claim 2, wherein the carrier structure is disk shaped.

18. The cartridge of claim 2, wherein the wherein the cavity has a first planar surface, and wherein the container has a second planar surface.

19. The cartridge of claim 18, wherein the first frictional element is formed on the first planar surface, wherein the second frictional element is formed on the second planar surface, wherein the first frictional element and the second frictional element are configured to remain in contact when the at least one container is rotated about the rotational axis.

20. The cartridge of claim 18, wherein the first planar surface is perpendicular to the rotational axis, wherein the second planar surface is perpendicular to the rotational axis.

21. The cartridge of claim 18, wherein the at least one container is constrained to rotate about the rotational axis such that the first planar surface and the second planar surface maintain a constant distance.

22. The cartridge of claim 2, wherein the piercing structure is arranged to pierce the pierceable seal perpendicular to the rotational axis.

23. The cartridge of claim 2, wherein the at least one container is constrained to enable only rotational motion about the rotational axis of the cartridge within the cavity.

24. The cartridge of claim 2, wherein the at least one container comprises a sidewall, and wherein the sidewall comprises the pierceable seal.

25. The cartridge of claim 24, wherein the pierceable seal and the rotational axis form an acute angle.

26. Automatic analyzer configured to receive a cartridge according to claim 2, wherein the automatic analyzer comprises a cartridge spinner, a rotational actuator, a measurement system, and a controller configured to control the automatic analyzer, wherein the controller is configured to:

rotate the at least one container relative to the carrier structure to open the pierceable seal using the rotational actuator;

control the rotational rate of the cartridge to process the biological sample into the processed biological sample using the fluidic structure by controlling the cartridge spinner;

control the rotational rate of the cartridge to force the at least one fluid through the duct and through at least a portion of the fluidic structure; and perform a measurement using the measurement structure and the measurement system.

* * * * *